(12) United States Patent
Gemmel et al.

(10) Patent No.: US 10,076,295 B2
(45) Date of Patent: Sep. 18, 2018

(54) MOBILE C-ARM SYSTEM

(71) Applicant: SIEMENS HEALTHCARE GMBH, Erlangen (DE)

(72) Inventors: Alexander Gemmel, Erlangen (DE); Sultan Haider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 107 days.

(21) Appl. No.: 15/092,846

(22) Filed: Apr. 7, 2016

(65) Prior Publication Data

US 2016/0296185 A1  Oct. 13, 2016

(30) Foreign Application Priority Data

Apr. 7, 2015  (DE) .......................... 10 2015 206 158

(51) Int. Cl.
*H05G 1/02* (2006.01)
*A61B 6/00* (2006.01)
*A61B 6/10* (2006.01)

(52) U.S. Cl.
CPC ............ *A61B 6/4441* (2013.01); *A61B 6/105* (2013.01); *A61B 6/4405* (2013.01); *A61B 6/547* (2013.01); *A61B 6/461* (2013.01)

(58) Field of Classification Search
CPC ....... A61B 6/4441; A61B 6/547; A61B 6/461; A61B 6/105
USPC ................................. 378/114–117, 193–198
See application file for complete search history.

(56) References Cited

U.S. PATENT DOCUMENTS

| 7,117,090 B2 | 10/2006 | Haider |
| 7,428,296 B2 | 9/2008 | Bernhardt et al. |
| 2013/0253485 A1 | 9/2013 | Fehre et al. |
| 2014/0314205 A1* | 10/2014 | Carelsen ................ A61B 6/461 378/62 |
| 2015/0065866 A1 | 3/2015 | Graumann et al. |
| 2016/0082596 A1* | 3/2016 | Barth ........................ B25J 5/00 700/255 |

FOREIGN PATENT DOCUMENTS

| DE | 102005023165 A1 | 11/2006 |
| DE | 102010027671 A1 | 1/2012 |
| DE | 102011078677 A1 | 10/2012 |
| DE | 102011082680 A1 | 3/2013 |

(Continued)

*Primary Examiner* — Courtney Thomas
(74) *Attorney, Agent, or Firm* — Laurence Greenberg; Werner Stemer; Ralph Locher

(57) ABSTRACT

A mobile C-arm system contains a main unit having a relocation apparatus for moving the main unit in a horizontal movement direction and a C-arm which is movable at least in the orbital and angular movement direction, a data processing unit having a memory for storing programs which are executed during operation, and a control and display system, connected to the main unit with operating and display elements. A plurality of sensors are provided for capturing at least part of the immediate environment of the C-arm. A control system is present, which is configured to warn against an obstacle in the intended or actual movement direction on the basis of the environment captured by at least one sensor, in dependence on an intended or actual movement of the main unit and/or at least part of the main unit in a movement direction.

16 Claims, 5 Drawing Sheets

(56) References Cited

FOREIGN PATENT DOCUMENTS

| | | |
|---|---|---|
| DE | 102012202359 A1 | 8/2013 |
| DE | 102012213202 A1 | 1/2014 |
| DE | 102012217173 A1 | 4/2014 |
| DE | 102013209769 A1 | 11/2014 |
| DE | 102013215445 A1 | 2/2015 |
| DE | 102013217476 A1 | 3/2015 |

* cited by examiner

MOBILE C-ARM SYSTEM

CROSS-REFERENCE TO RELATED APPLICATION

This application claims the priority, under 35 U.S.C. § 119, of German application DE10 2015 206 158.2, filed Apr. 7, 2015; the prior application is herewith incorporated by reference in its entirety.

BACKGROUND OF THE INVENTION

Field of the Invention

The invention relates to a mobile C-arm system having in particular a main unit that is equipped with a relocation apparatus and a C-arm which is movable in the orbital and angular movement direction, a data processing unit having a memory, a control and display system, connected to the main unit of the C-arm system, with operating and display elements, and a plurality of sensors for capturing at least part of the immediate environment of the C-arm.

A mobile C-arm system is known, for example, from document published, non-prosecuted German patent application DE 10 2012 202 359 A1. This document describes a mobile C-arm system having an emitter/detector arrangement mounted on a C-arm, consisting of an X-ray tube mounted at one end of the C-arm and a first flat panel detector mounted to the other end of the C-arm, wherein furthermore provided is a control and computing system for operating the C-arm system including image data acquisition.

Furthermore known from published, non-prosecuted German patent application DE 10 2005 023 165 A1, in connection with a medical imaging system, is a collision protection method, in which a part that is displaceable around a patient for preventing collision of the displaceable part with the patient is used to stop or slow the movement of the displaceable part if the part enters a protection zone enveloping the patient. The surface of the patient is previously optically captured and an individual protection zone for the patient is computed from the captured surface of said patient.

Published, non-prosecuted German patent application DE 10 2012 217 173 A1 discloses a mobile C-arm system which is detected, with the aid of radio-frequency transmitters mounted on the apparatus and antennas arranged in the environment, with respect to the positioning thereof in the environment. Wherein collision prevention with respect to known fitments in the correspondingly equipped environment is provided. The disadvantage of this system is that the mobile C-arm system can move reliably only in an environment that is correspondingly provided with radio-frequency receivers.

Published, non-prosecuted German patent application DE 10 2011 078 677 A1 discloses a stationary C-arm system that is mounted fixedly to the underlying area and has a C-arm which is variable with respect to the radius thereof, wherein it is noted that the C-arm can have a collision detection apparatus for the movements of the C-arm.

Reference is furthermore made to published, non-prosecuted German patent applications DE 10 2011 082 680 A1, DE 10 2010 027 671 A1 and DE 10 2012 213 202 A1, which disclose general prior art relating to C-arm systems.

However, such systems in principle retain the problem that any manual movement or control of a mobile C-arm system when displacing the system between different sites of use is associated with the risk of collision, in particular that the detector arranged at the C-arm and X-ray tube can result in collisions with fitments. If such a collision occurs, considerable damage can result, and also considerable loss of time owing to a restart of the system which may become necessary, which may even have lethal consequences in the case of the imminent examination of an emergency patient.

SUMMARY OF THE INVENTION

It is therefore the object of the invention to find a C-arm system which avoids collisions with objects located in the surrounding area or at least aids in reducing such collisions strongly.

The object is achieved by way of the features of the independent patent claims. Advantageous developments of the invention are subject matter of dependent claims.

It has been found that it is possible in a mobile C-arm system—such as for example the Cios Alpha or the ARCADIS by the applicant—which has at least a relocatable main unit having a C-arm which is also movable separately, a likewise relocatable control and display system and, if appropriate, also an additional freely movable control and display tablet, to prevent collisions using environment information ascertained by sensors that are affixed to the main unit by warning against an obstacle in the intended or actual movement direction on the basis of the environment captured by the at least one sensor in dependence on an intended or actually already occurring movement of the main unit and/or of the C-arm, which is part of the main unit, in a movement direction of at least a part of the C-arm system.

Such a warning can initially be in the display of the environment in the movement direction. The occurrence and of course the detection of an actual movement in a movement direction—preferably with the aid of a movement sensor—can be used as a trigger for the corresponding display of the surrounding area of the moving part in the movement direction. If a control is present, for example in connection with actuation by motor, it is possible for a control command for moving the main unit or the C-arm—preferably on a program-technological level, if appropriate by way of a control command which has not yet been executed or confirmed—to be the trigger for the display in the intended movement direction.

Such a display can be effected preferably on the control and display system and/or on the control and display tablet which may also additionally be present.

As soon as a movement is effected or taking place, it is possible for example for at least one corresponding window on a display apparatus, at which the respective movement control takes place, to open such that the operator initiating the movement immediately has a corresponding overview of the surrounding area in which the movement is effected or is to be effected. As a result, the operator also sees environment regions which are actually not within his field of vision, for example a region underneath a patient bed or a region which is covered against the field of vision of the operator by any objects or persons.

It can be expedient in principle to provide different display situations, depending on the type of movement or of the moving part. If the entire main unit is relocated or the movement is a horizontal movement, it may be particularly expedient to represent a display from a bird's eye perspective which comes about, if appropriate, by combining the information from a plurality of sensors, preferably cameras. This can be a 360° around view or merely a view from above in the movement direction, in each case with a—possibly virtual—representation of the main unit and of the detected environment. The represented plane is here in each case oriented horizontally.

On the other hand, in the case of a reaction to an intended or occurring separate movement of the C-arm, it may be advantageous to represent an intended rotational movement in the plane of rotation thereof or the orbital plane of the C-arm. However, it is also possible, if appropriate, for combinations of the previously mentioned planes, preferably in a plurality of windows, to be displayed on a display.

In addition to the pure representation of the environment or of an environment region, it is also advantageously possible for obstacle detection to be carried out on the basis of available image information which can, if appropriate, also be 3D image information, and/or with the aid of additional sensors. To this end, TOF sensors (TOF=time of flight), ultrasound distance sensors, which can preferably be attached to the main unit and/or to the C-arm, can be used.

With respect to the attachment of the sensors, in particular of the cameras, it is particularly advantageous if they are attached to the housing of the main unit and are equipped with a recording angle such that a preferably gap-free 360° around view image can be assembled at least at one height. The attachment of the sensors and/or cameras can also take place advantageously in at least two planes of different heights, preferably also parallel. Furthermore, the sensors and cameras can be arranged at the C-arm, in particular in the region of the detector and the X-ray tube. By way of example, the sensors/cameras can be attached at the detector and at the X-ray tube such that for all movements able to be effected by the C-arm, likewise a forward-looking representation of the environment in the respective movement direction is possible. This applies in particular also to any movement in the vertical movement direction of the C-arm, for example by attaching the sensors or cameras in the outer and inner region of the circumference of the C-arm.

With respect to the configuration of sensors or cameras used, it appears to be particularly expedient to integrate them in the respective surfaces such that, in the case of cameras, only the surface of a lens, in particular a wide-angle lens, and in the case of other sensors, the sensor surface protrudes as little as possible from the surface of the respective cover of the main unit or of the C-arm.

In supplementation to a mere display of the relevant environment region for the purposes of warning against possible obstacles, it is additionally also possible to visually highlight an intended or actual movement space that contains an obstacle, wherein the highlighting can be for example in the form of corresponding coloration or addition of a background, preferably in red, or by way of a flashing display. Alternatively or in supplementation, however, it is also possible to display a movement space which is positively free of obstacles by way of a corresponding visual representation, addition of a background for example in color, preferably green or yellow, or in particular light-colored representation. Another possibility is to vary the coloration of a respective movement sector in the movement direction depending on the distance to a nearest obstacle.

The display per se can be effected in one or more respectively opening or already present windows on one or more display apparatuses, with touch screens possibly also being advantageous for this purpose.

It is also possible for an acoustic or haptic signal to be output to the operator as the warning, wherein this signal can also be output specifically with respect to direction and/or distance from an identified obstacle.

According to one additional aspect of the invention, it was also recognized that, in addition to the warning with respect to a potential obstacle, it is also possible to avoid collision with an obstacle by way of an intervention in the possible movement states of the C-arm system or a part thereof.

In the case of manually driving the movement of the main unit or of the C-arm, a potentially collision-producing movement can, in the simplest case, be braked or stopped by way of automatic actuation of a brake apparatus. With respect to the mobile displace ability of at least the main unit, it is possible, for example, for a brake to be arranged on the wheels or rollers thereof, or brake apparatuses can be mounted independently of the wheels and rollers—for example by way of friction blocks acting directly on the ground—which are actuated automatically in the case of an imminent collision.

However, in the case of a drive for displacing the main unit by motor or for moving the C-arm by motor, it is possible to intervene in the driving when an obstacle is identified such that a collision is prevented. The intervention preferably takes place on a program-technological level by overdriving a program-controlled command for moving at least part of the main unit and by braking or stopping the movement in a program-controlled manner.

In supplementation, it is proposed that the operator is given the possibility to overdrive a cessation of the movement of at least part of the main unit using a super ordinate command and still allow a driven movement or release of the brakes even in the case of imminent collision, for example when relocating through very narrow doors or if the C-arm is intended to be relocated closely to an obstacle.

It should be noted that these exemplary embodiments described above and the features thereof can be realized according to the invention individually or in combination, not only in connection with a C-arm system according to the preamble of the application, but also with mobile C-arm systems generally.

According to the previously explained basic concept of the invention, various exemplary embodiments according to the invention and combinations thereof are proposed, wherein it should be noted that the characterizing features are part of the invention also generally in connection with a mobile C-arm system without the additional features of the preamble.

What is proposed is thus a mobile C-arm system, containing:
a) a main unit having a relocation apparatus for moving the main unit in a horizontal movement direction and a C-arm which is movable at least in the orbital and angular movement direction, preferably including a C-arm drive;
b) a data processing unit having a memory for storing programs which are executed during operation;
c) a control and display system, connected to the main unit of the C-arm system, with operating and display elements;
d) wherein according to the invention, a plurality of sensors are present for capturing at least part of the immediate environment of the C-arm; and
e) a control system is present in the C-arm system, which is configured to warn against an obstacle in the intended or actual movement direction on the basis of the environment captured by at least one sensor arranged at the C-arm system, in dependence on an intended or actual movement of the main unit.

The sensors which can be used for capturing at least part of the immediate environment of the C-arm system can in principle be all sensors which allow for information regarding the spatial configuration of the environment to be obtained. By way of example, this relates to ultrasound or infrared sensors which can ascertain at least a distance to an obstacle. Likewise used can be optical sensors, for example 2D or 3D cameras, or TOF sensors, which permit the establishment of a three-dimensional representation of the surrounding surfaces within the capturing region of the TOF sensor. Such sensors are in connection with optical cameras in the KINECT systems which are used in games consoles for capturing players and their environment. Corresponding GUIs are generally accessible herefor. Also proposed accordingly is that at least one of the sensors is a sensor type from the following list: ultrasound sensor, infrared sensor, TOF sensor (TOF=time of flight), optical sensor, 3D camera.

Also proposed is that the control system of the C-arm system is configured such that an image of the environment in the movement direction recorded by at least one of the sensors is displayed on at least one display element to warn against an obstacle. What should be noted here is that the displayed image does not necessarily have to come from a single camera, it is also possible for an environment image to be generated over a large solid angle and, if appropriate, for only a collision-technologically relevant sector to be displayed by way of combining the sum of information from a plurality of sensors arranged at the C-arm system.

Preferably, a region that is at risk of collision can be additionally represented on the displayed image of the environment such that it is visually highlighted.

Since a mobile C-arm system having a relocation apparatus, that is to say for example a frame having wheels or rollers which permit only limited movement profiles, has uniquely defined movement spaces to be used, it may be particularly expedient when displaying the environment in the movement direction to give visual prominence exactly to these possible movement spaces. It is correspondingly proposed here that the mobile C-arm system has a control system which is configured such that a movement region that is subject to control is displayed in a representation of the environment.

To support the collision avoidance, the control system of a mobile C-arm system can be configured such that a movement region that is subject to control and in which a risk of collision is detected is visually highlighted in a representation of the environment. This can be done in the display for example by way of the addition of a colored background or a, preferably colored, border or else by symbolic representation of the movement direction by way of, preferably colored, arrows. With respect to the identification of possible obstacles, it is possible here for example to use pattern recognition, preferably in the image representations, or to use information from a 3D camera, TOF sensors or ultrasound sensors.

Alternatively or in supplementation, it is also within the scope of the invention for the control system to be configured such that a movement region that is subject to control and is identified as collision-free is visually highlighted in a representation of the environment, preferably by, preferably green, coloration or a colored border or colored arrows.

Furthermore, in a C-arm system according to the invention, the control system can also be configured such that in the case of a relatively approaching obstacle, an acoustic and/or a haptic warning signal is output, preferably in dependence on the direction and distance of the obstacle to at least part of the C-arm system. With respect to the haptic signal, it can be expedient here for this to be transmitted to the operator via at least one operating element, for example by way of vibration of a push handle or joystick. If the haptic signal is in the form of vibrations, it is possible for example for the frequency and/or amplitude of the vibrations to vary with the distance of the obstacle, preferably act inversely proportionally to the distance, or to represent a function of distance and approach speed to the obstacle.

It can also be advantageous to design the C-arm system, in particular the control system, such that in the case of an intended or actual movement of the main unit, a 360° around view from the captured information from a plurality of sensors from a perspective of above the main unit including a, preferably virtual, representation of the main unit is displayed in at least one display element. Such a display allows the operator to identify the obstacle-relevant environment situation from the bird's eye perspective.

It can be advantageous here in the representation of obstacles to highlight them visually, preferably in color, wherein optionally the intensity of the highlighting can be adjusted in dependence on the distance or on the collision probability as a function of the movement speed, the movement direction and the distance. Accordingly, the control system can also be configured such that in the around view image, those sectors are visually highlighted, preferably in color, in which an obstacle falls below a prespecified distance, preferably a distance which is dependent on the approach speed to the obstacle.

One further variant for avoiding collisions, specifically of the C-arm, can be to design the control system such that, in the case of a detected approach of the C-arm to an obstacle, the control of the C-arm is influenced in a superordinate fashion such that a collision is avoided.

In a further embodiment of the C-arm system, it is proposed in a mobile C-arm system—even if it has no dedicated drive—for the main unit to be equipped with an automatically controllable brake system and for the control system to be configured such that in the case of a manual movement of the main unit in the case of a detected approach of the main unit to an obstacle, the brake system is influenced in a super ordinate fashion such that a collision is avoided. Such super ordinate influencing can mean that simply the entire movement, preferably up to a complete standstill, is braked or that by selective operation of individual brake elements, directional control is effected which guides the main unit past the identified obstacle.

Yet another embodiment of a mobile C-arm system, preferably of a mobile C-arm system according to a previously described embodiment with the exception of the embodiments which are configured explicitly without a drive, makes provision for the main unit to have a dedicated drive for motor-operated advancement and for the control system to be configured such that in the case of advancement of the main unit in the case of a detected approach of the main unit to an obstacle, the drive of the main unit is influenced in a superordinate fashion such that a collision is avoided.

Other features which are considered as characteristic for the invention are set forth in the appended claims.

Although the invention is illustrated and described herein as embodied in a mobile c-arm system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The invention will be described in more detail below with reference to preferred exemplary embodiments with the aid of the figures, wherein only the features that are necessary for understanding the invention are represented. Here, reference symbols with these following meanings are used: 1: main unit of a C-arm system; 1.1: combined display and operating apparatus; 1.2: wheels; 2: C-arm; 3: X-ray tube; 4: detector; 5: monitor trolley; 5.1: screen; 5.2: screen; 5.3: operating field; 5.4: computer system; 5.5: memory; 5.6: control system; 6: patient bed; 6.1: supporting foot; 8: heart-lung machine; a: angular direction; bg: green region; br: red region; by: yellow region; h: vertical movement direction; o: orbital direction; s: horizontal movement direction; x, y: Cartesian coordinates; A: doctor; B1, B2: movement regions; C: region at risk of collision; F: window; K: nurse; $P_1$-$P_n$ software/program; P1-P4: paths; S: environment sensors.

Figure 1:
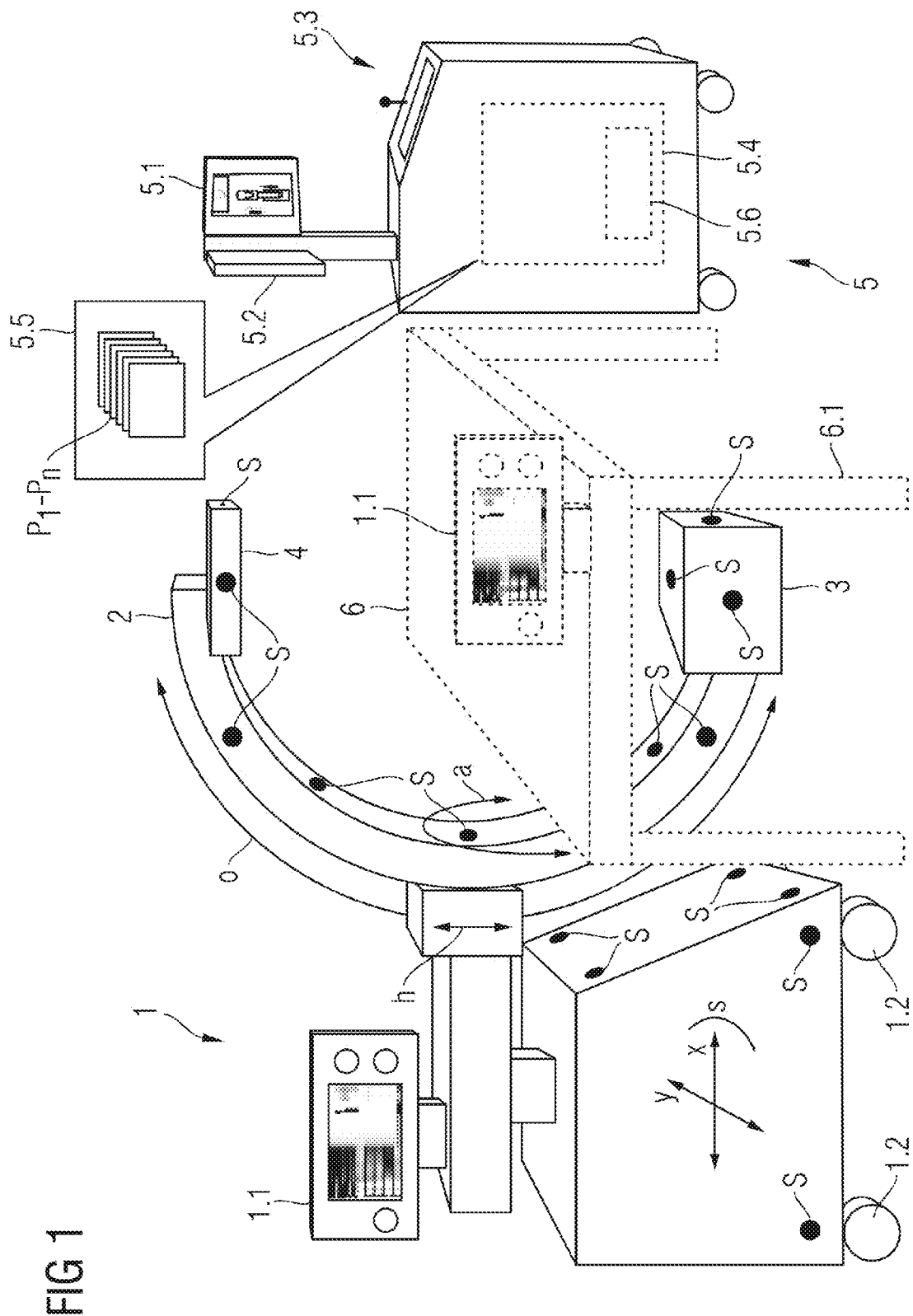
FIG. 1 is a diagrammatic, perspective view of a mobile C-arm system according to the invention having a main unit and a monitor trolley and an optional operating tablet.

Referring now to the figures of the drawings in detail and first, particularly to FIG. 1 thereof, there is shown a typical setup of a mobile C-arm system according to the invention having the main unit 1, which is displaceable on wheels 1.2 that are driven by way of a motor and controllable, if appropriate, and on which a C-arm 2 is located with an X-ray tube 3 and a detector 4 arranged at one end side each. The C-arm 2 is mounted, and provided with a drive (not visible here), such that it can carry out the typical movements in the angular direction a, in the orbital direction o and in the vertical movement direction h, without moving the entire main unit. The horizontal movement directions x, y, s are here effected by way of manual or motorized gliding or pivoting of the entire main unit 1. To operate the main unit 1, a combined display and operating apparatus 1.1 is located thereon, which in one optional embodiment can also be removed from the main unit 1 and, for example, be mounted on a patient bed. The necessary data is here transmitted preferably wirelessly, for example via Bluetooth or WLAN.

Also part of the C-arm system is what is referred to as the monitor trolley 5, on which the control and display apparatuses are located which are to be operated and observed in particular by an examining doctor. In the exemplary embodiment illustrated here, the monitor trolley 5 has two screens 5.1 and 5.2, which are used primarily for displaying examination parameters and examination results. Also located on the monitor trolley 5 is an operating field 5.3 with a joystick for inputting necessary recording parameters and control commands. In principle, the entire C-arm system can here be constructed such that all inputs and control commands necessary for carrying out an examination can be undertaken at each operating unit in a system-wide fashion. The screens and the operating interfaces used here can be conventional displays, mechanical operating elements (e.g. push buttons, joysticks), touch pads or touch screens, which are also operated, if appropriate, via gesture control. Combinations of the above-mentioned display and operating elements likewise fall within the scope of the invention.

Also located in the monitor trolley 5 in the illustrated exemplary embodiment is a computer system 5.4 having a control system 5.6, in the memory 5.5 of which programs $P_1$ to $P_n$ are stored, which during operation also assume the control of the C-arm system, the evaluation of the detector data necessary for displaying X-ray recordings, and also perform method steps according to the invention. However, it should be noted that the positioning of the computer system is not necessarily limited to the monitor trolley 5. It is likewise possible for the computer system to be arranged in the main unit 1 or to be implemented in decentralized fashion in both units, without departing from the scope of the invention.

FIG. 1 additionally shows an exemplary patient bed 6 having four legs 6.1 arranged at the corners, wherein both the resting surface and the legs could lead to collisions for the C-arm system in case of careless movement of the C-arm 2 or of the entire main unit 1.

A plurality of sensors S are arranged on the main unit according to the invention to avoid possible collisions, which sensors S can in turn contain individual sensors of various types, for example optical cameras, preferably having wide-angle lenses, preferably enclosing a solid angle of 180°, with ultrasound sensors, IR sensors, electromagnetic sensors or TOF sensors.

The control system 5.6 can be used to prepare, by way of corresponding programs $P_1$-$P_n$ global information relating to existing obstacles in the movement region of the main unit 1 including the C-arm 2, which information is obtained using some or all the information relating to the spatial environment configuration that is gathered by the sensors S, such that, with the knowledge of an intended movement direction, corresponding warnings are output in the manner that is described in more detail above. In particular, the immediate environment in the movement direction can be displayed on one or more display apparatuses of the C-arm system, wherein preferably regions that are at risk of collision can be represented such that they are visually highlighted for warning purposes. By contrast, it is also possible to visually highlight a collision-free movement region separately, such that the operating staff can move the main unit 1 of the C-arm system within this region with a great degree of safety.

In the situation illustrated in FIG. 1, it is possible for example for the sensors S arranged at the bottom at the front of the main unit 1 to also identify the spatial relationships below the patient bed 6, while a doctor standing on the other side of the patient bed 6 at the monitor trolley 5 cannot see, within his immediate field of vision, the situation there or the freedom of movement or the obstacles located there. If—as can be the case in a C-arm system according to the invention, for example—the movement of the main unit 1 is controlled in the direction toward the patient bed, it is possible to display on one of the screens 5.1 or 5.2 immediately the region below the patient bed 6 with the lower part of the C-arm 2 located there and/or to display, if appropriate, any obstacles. It is also possible using visual, acoustic and/or haptic measures to signal whether an intended movement is free of obstacles.

Also within the scope of the invention is a continuous measurement and updating of the environment situation such that a current representation of the environment situation is always ensured.

Figure 2:
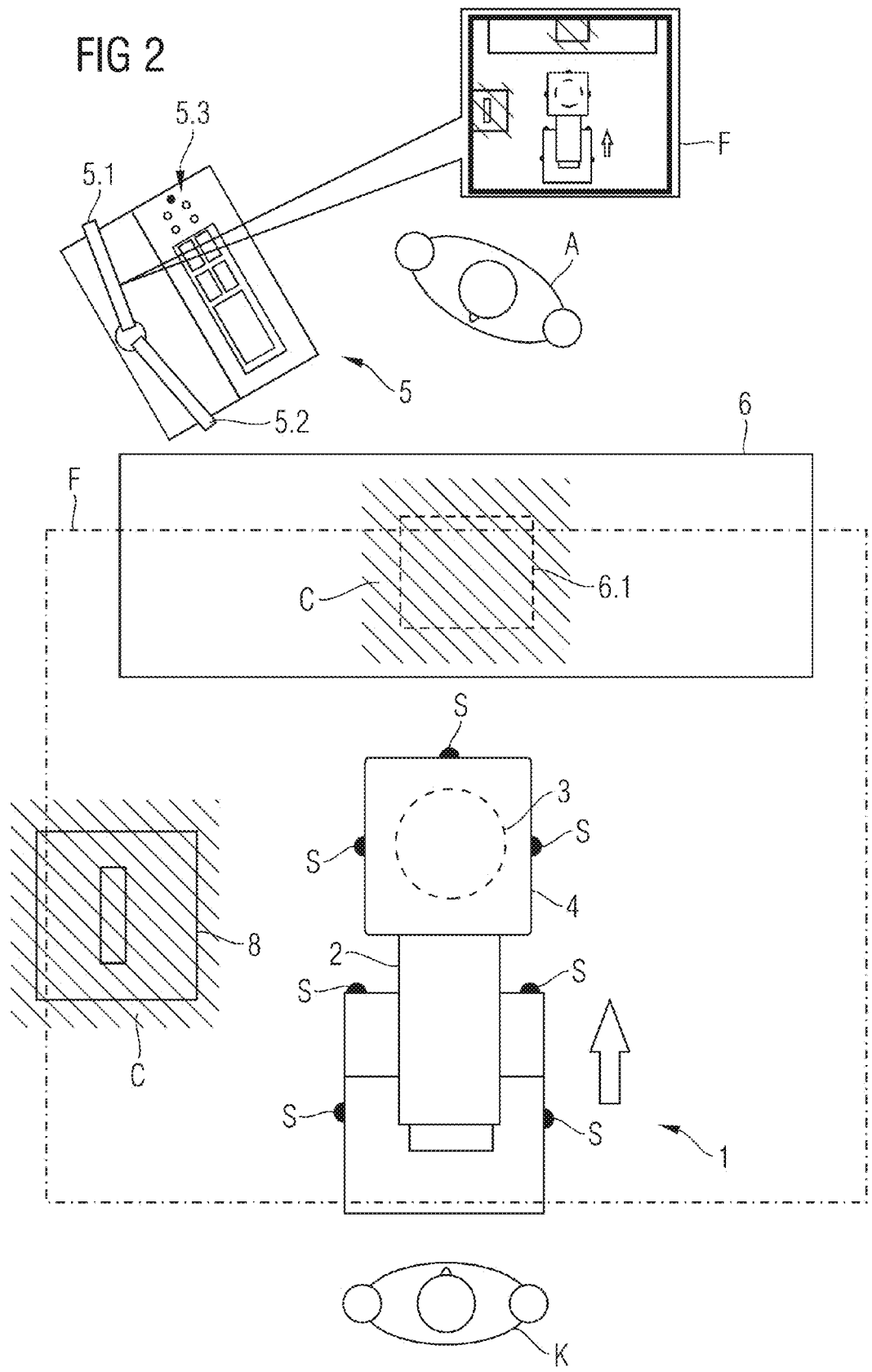
FIG. 2 is a plan view of the mobile C-arm system according to the invention having the main unit and the monitor trolley including representation of regions that are at risk of collision in current C-arm position.

FIG. 2 illustrates in plan view from above a similar situation in an operating room, using the same reference symbols, wherein the room additionally contains, in addition to the main unit 1 of the C-arm system, a heart-lung machine 8, serving as an example of an obstacle, and the patient table has a supporting foot 6.1 located centrally under the table. Additionally illustrated are an assisting nurse K at the main unit 1 and a doctor A at the monitor trolley 5. In the situation illustrated, the main unit 1 has the C-arm 2 in a perpendicular park position such that the resting surface of the patient bed 6 itself is not considered an obstacle for the C-arm 2 which protrudes to the front with the detector 4 and the X-ray tube 3 located there. The regions C that are at risk with respect to a collision are illustrated in the display in hatched fashion, preferably with a red background. If the main unit 1 is moved further to the front, such that the distance in the plane of the resting surface of the patient bed 6 falls below a safety distance, this resting surface is also illustrated in hatched fashion or in red.

The representation shown on a display apparatus, preferably in a window of the display apparatus, for example one of the screens 5.1, 5.2 or 1.1, according to the invention, here corresponds to the content of the window F which has a dashed border and is shown again in the speech bubble on the screen 5.1. What should be noted here is that, owing to the environment sensors S attached at the main unit 1, of course only those sides of an obstacle can be shown that are visible to the sensors.

At the same time, it is also possible for a further window to open on the screen selected for such display, in which window a horizontal view in the movement direction is shown in which the main unit 1 moves or is intended to move. Here the regions C that are at risk of collision can also be visually highlighted, with it being essential that a visible difference between the visual illustration of regions that are at risk of collision and the collision-free regions is produced.

Figure 3:
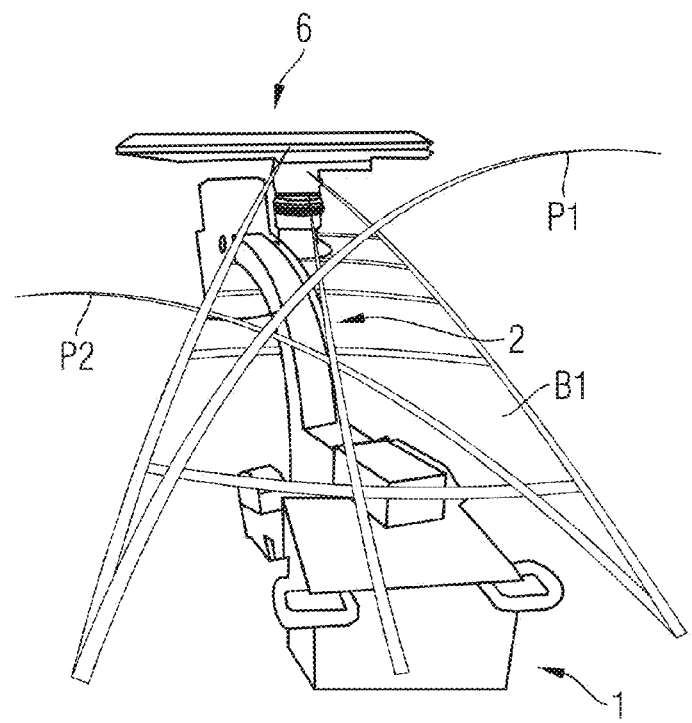
FIGS. 3-4 are perspective views showing examples of display representations with forward-looking views of collision-free movement regions and movement paths and movement regions and movement paths that are at risk of collision of the main unit with C-arm.
Figure 4:
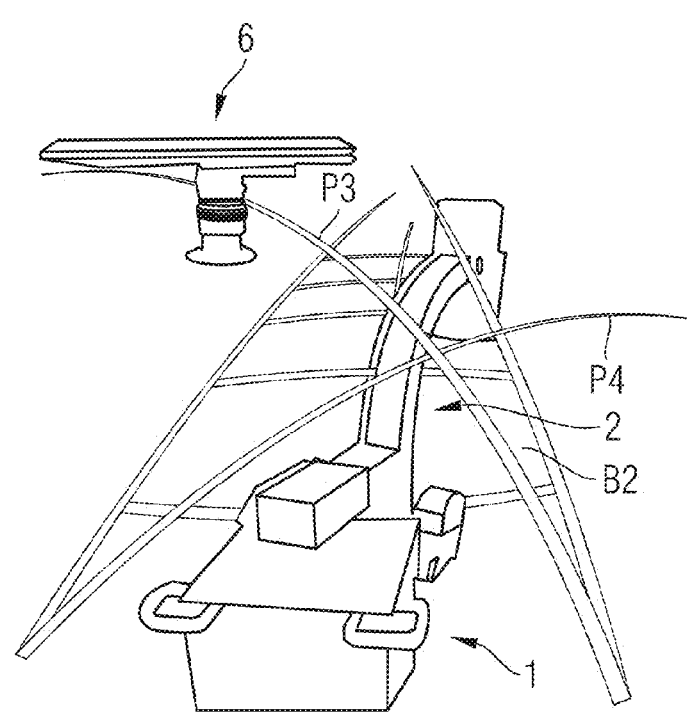

FIGS. 3 and 4 show two similar situations of the movement of a C-arm system with the main unit 1 and the C-arm 2 as a view on a screen, wherein additionally the ascertained paths P1, P2 and movement regions B1 and B2 are shown. FIG. 3 shows a movement region B1 which is not free of collision, while the paths P1 and P2 in each case allow collision-free movement. According to the invention, the non-collision-free region B1 can be represented in a display in red or have a red background, while the paths P1 and P2 could be represented, for example, in green. By contrast, in FIG. 4, the movement region B2 is free of collisions, assuming the C-arm remains in the current position, such that this region could be represented in green. By comparison, path P3 results in a collision of the C-arm 2 with the patient bed 6 and is therefore represented in a warning color, typically red. The path P4 guides the C-arm 2 out of the collision region and therefore has a green background, for example.

Figure 5:
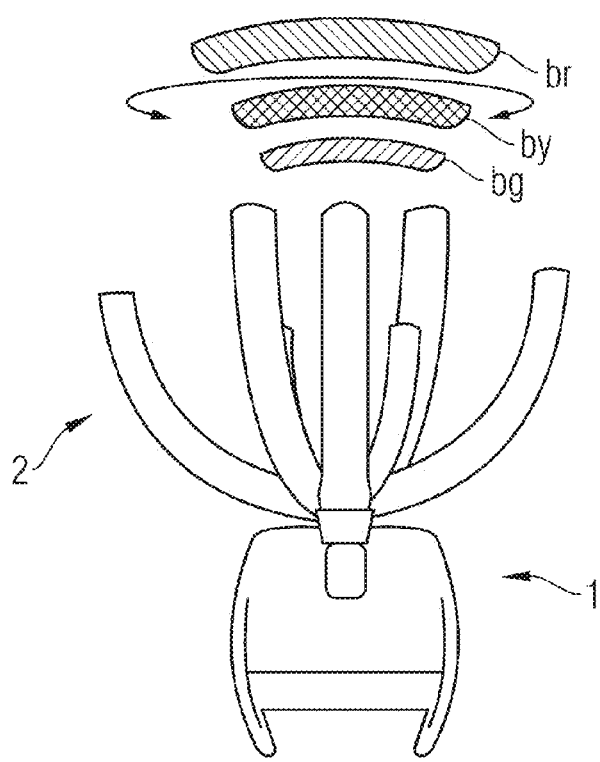
FIGS. 5-6 are illustrations showing examples of display representations with forward-looking views of collision-free movement regions and movement regions that are at risk of collision of the main unit with C-arm.
Figure 6:
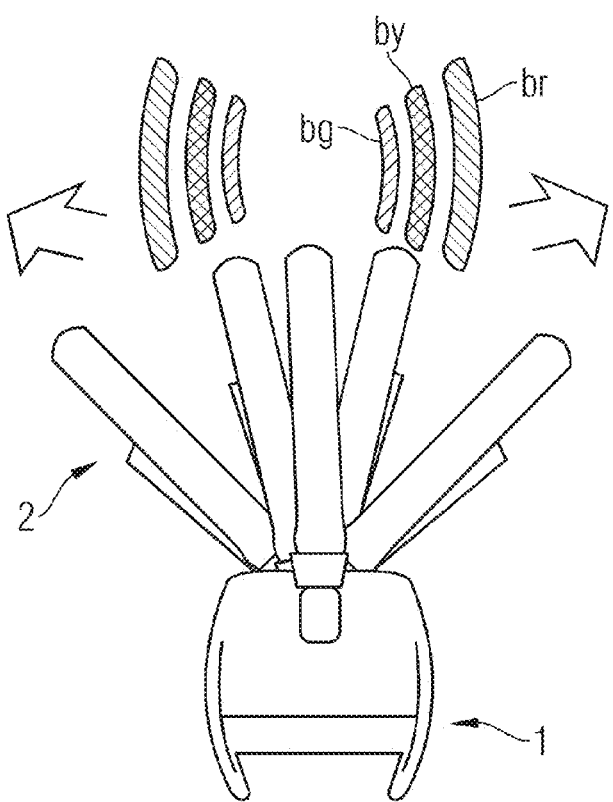

FIGS. 5 and 6 visualize a representation of two movement situations of the C-arm 2 itself on one display apparatus. FIG. 5 illustrates the intended angular movement of the C-arm 2, with three regions br (red), by (yellow) and bg (green) being represented, which have backgrounds according to their schematically illustrated angle of rotation in the colors green for collision-free, yellow as the attention region for reduced movement speed and increased caution, and red for the collision region. Accordingly, FIG. 6 illustrates an example of a pivot movement, wherein the regions having a red br, yellow by and green bg background are also illustrated here schematically. Corresponding representations can also be displayed for all other possible movements, in particular also orbital movements.

Figure 7:
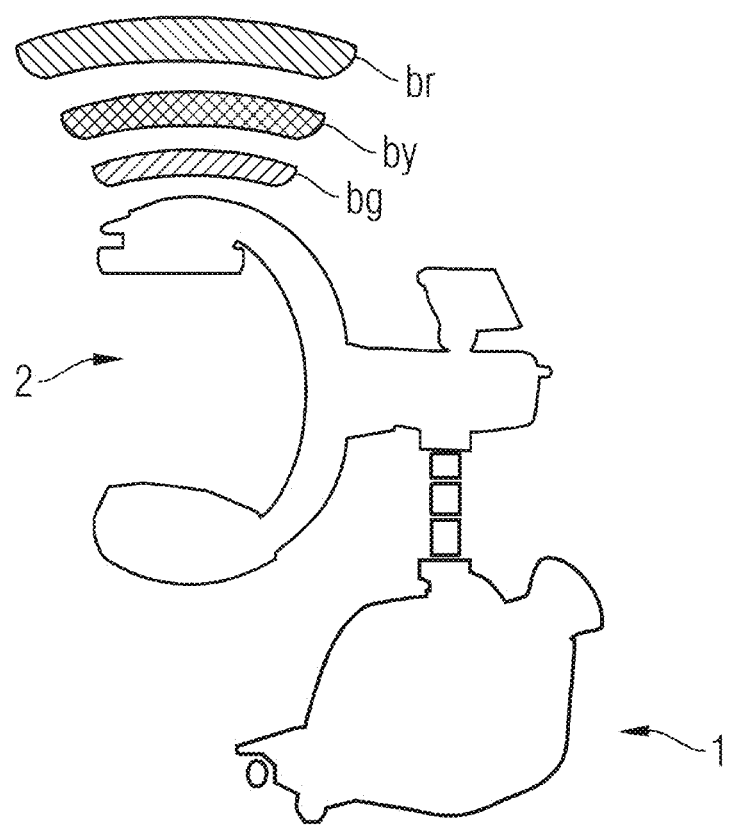
FIG. 7 is an illustration showing a representation of an exemplary collision warning relating to the vertical movement of the C-arm.

In FIG. 7, ultimately a corresponding schematic display for an intended vertical movement of the C-arm 2 on the main unit 1 is shown, wherein the colors from FIGS. 4 to 6 are used again here.

Overall, the invention thus proposes a C-arm system in which a control system is present which is configured to warn against an obstacle in the intended or actual movement direction on the basis of the environment captured by at least one sensor, in dependence on an intended or announced or actual movement of the equipment carrying the C-arm and/or at least part of the C-arm system, such as the C-arm itself.

Even though the invention has been illustrated and described in detail by way of the preferred exemplary embodiment, the invention is not limited by the disclosed examples, and other variations can be derived therefrom by the person skilled in the art, without departing from the scope of protection of the invention.

The following is a summary list of reference numerals and the corresponding structure used in the above description of the invention:

1: main unit of a C-arm system
1.1: combined display and operating apparatus
1.2: wheels
2: C-arm
3: X-ray tube
4: detector
5: monitor trolley
5.1: screen
5.2: screen
5.3: operating field
5.4: computer system
5.5: memory
5.6: control system
6: patient bed
6.1: supporting foot
8: heart-lung machine
a: angular direction
bg: green region
h: vertical movement direction
o: orbital direction
br: red region
s: horizontal movement direction
by: yellow region
x: horizontal movement direction
y: horizontal movement direction
A: doctor
B1: movement region
B2: movement region
C: region at risk of collision
F: window
K: nurse P1: path
P2: path
P3: path
P4: path
S: environment sensors
P$_1$-P$_n$ software/programs

The invention claimed is:

1. A mobile C-arm system, comprising:
   a main unit having a relocation apparatus for moving said main unit in a horizontal movement direction and a C-arm being movable at least in an orbital and angular movement direction;
   a data processing unit having a memory for storing programs executed during operation;
   a control and display system connected to said main unit and having display elements;
   a plurality of sensors for capturing at least part of an immediate environment of said C-arm; and
   a control system configured to warn against an obstacle in an intended or actual movement direction on a basis of the immediate environment captured by at least one of said sensors in dependence on an intended or actual movement of said main unit.

2. The mobile C-arm system according to claim 1, wherein at least one of said sensors is a sensor type selected from the group consisting of an ultrasound sensor, an infrared sensor, a time of flight sensor, an optical sensor and a 3D camera.

3. The mobile C-arm system according to claim 1, wherein said control system is configured such that an image of the immediate environment in the movement direction recorded by at least one of said sensors is displayed on at least one of said display elements to warn against the obstacle.

4. The mobile C-arm system according to claim 3, wherein said control system is configured such that a region that is at risk of collision is additionally represented on an image such that it is visually highlighted.

5. The mobile C-arm system according to claim 1, wherein said control system is configured such that a movement region that is subject to control is displayed in a representation of the immediate environment.

6. The mobile C-arm system according to claim 1, wherein said control system is configured such that a movement region that is subject to control and in which a risk of collision is detected is visually highlighted in a representation of the immediate environment.

7. The mobile C-arm system according to claim 1, wherein said control system is configured such that a movement region that is subject to control and is identified as collision-free is visually highlighted in a representation of the immediate environment by coloration, a colored border or colored arrows.

8. The mobile C-arm system according to claim 1, wherein said control system is configured such that in a case of a relatively approaching obstacle, at least one of an acoustic or a haptic warning signal is output.

9. The mobile C-arm system according to claim 1, wherein said control system is configured such that in a case of the intended or actual movement of said main unit, a 360° around view from captured information from a plurality of said sensors from a perspective of above said main unit including a representation of said main unit is displayed in at least one of said display elements.

10. The mobile C-arm system according to claim 9, wherein said control system is configured such that in an around view image, sectors are visually highlighted, in which an obstacle falls below a prespecified distance.

11. The mobile C-arm system according to claim 1, wherein said control system is configured such that, in a case of a detected approach of said C-arm to the obstacle, a control of said C-arm is influenced in a super ordinate fashion such that a collision is avoided.

12. The mobile C-arm system according to claim 1, wherein:
   said main unit has an automatically controllable brake system; and
   said control system is configured such that in a case of a manual movement of said main unit in a case of a detected approach of said main unit to the obstacle, said automatically controllable brake system is influenced in a super ordinate fashion such that a collision is avoided.

13. The mobile C-arm system according to claim 1, wherein:
   said main unit has a dedicated drive for motor-operated advancement; and
   said control system is configured such that in a case of advancement of said main unit in a case of a detected approach of said main unit to the obstacle, said dedicated drive of said main unit is influenced in a super ordinate fashion such that a collision is avoided.

14. The mobile C-arm system according to claim 1, wherein said control system is configured such that in a case of a relatively approaching obstacle, at least one of an acoustic or a haptic warning signal is output in dependence on a direction and distance of the obstacle to at least part of said main unit.

15. The mobile C-arm system according to claim 9, wherein said control system is configured such that in an around view image, sectors are visually highlighted in color, in which an obstacle falls below a prespecified distance dependent on the approach speed.

16. A mobile C-arm system, comprising:
   a main unit having a relocation apparatus for moving said main unit in a horizontal movement direction;
   a C-arm mounted to, and transportable by, said main unit, said C-arm being movable at least in an orbital and angular movement direction;
   a data processing unit having a memory for storing programs executed during operation;
   a control and display system connected to said main unit and having display elements;
   a plurality of sensors mounted to a body of said main unit for capturing at least part of an immediate environment of said main unit; and
   a control system configured to warn against an obstacle in an intended or actual movement direction of said main unit, on a basis of the immediate environment captured by at least one of said sensors in dependence on an intended or actual movement of said main unit.

* * * * *